United States Patent [19]

Vailancourt

[11] Patent Number: 4,705,709
[45] Date of Patent: Nov. 10, 1987

[54] LUBRICANT COMPOSITION, METHOD OF COATING AND A COATED INTUBATION DEVICE

[75] Inventor: Vincent L. Vailancourt, Livingston, N.J.

[73] Assignee: Sherwood Medical Company, St. Louis, Mo.

[21] Appl. No.: 781,218

[22] Filed: Sep. 25, 1985

[51] Int. Cl.$^4$ ............... A61M 5/325; A61M 25/005; A01N 1/02
[52] U.S. Cl. ................................. 428/36; 252/50; 427/2; 604/265
[58] Field of Search ............ 427/2; 428/36; 604/265; 252/50

[56] References Cited

U.S. PATENT DOCUMENTS

| | | | |
|---|---|---|---|
| 3,822,238 | 7/1974 | Blair et al. | 106/13 X |
| 3,975,350 | 8/1976 | Hudgin et al. | 428/425 X |
| 4,278,633 | 7/1981 | Fujii | 264/134 |
| 4,388,076 | 6/1983 | Waters | 604/283 X |
| 4,525,374 | 6/1985 | Vaillancourt | 427/2 |
| 4,536,179 | 8/1985 | Anderson | 604/266 |
| 4,548,844 | 10/1985 | Podell et al. | 427/2 X |
| 4,557,724 | 12/1985 | Gregonis et al. | 604/265 X |
| 4,581,390 | 4/1986 | Flynn | 428/36 X |

FOREIGN PATENT DOCUMENTS 0132387 1/1985 European Pat. Off. .
2912852 10/1980 Fed. Rep. of Germany .

OTHER PUBLICATIONS

Tergitol® NP Nonionic Surfactants, Union Carbide Corporation (1980) pp. 1-5.

Primary Examiner—Michael R. Lusignan
Attorney, Agent, or Firm—Kenyon & Kenyon

[57] ABSTRACT

The present invention is a lubricant coating composed of hydrophylic polymer and surfactant for intubation devices such as nasogastric tubes. The coating is strong and attains sufficient lubricity upon contact with water in less than about 5 minutes and preferably less than about 5 to 10 seconds to be used in intubation procedures.

22 Claims, 4 Drawing Figures

LUBRICANT COMPOSITION, METHOD OF COATING AND A COATED INTUBATION DEVICE

FIELD OF THE INVENTION

The present invention relates to a lubricant composition, a method of coating and a coated device. More particularly, the invention relates to lubricant coatings for medical devices, such as intubating devices, methods for coating such devices and the products thereof.

BACKGROUND OF THE INVENTION

Lubricant compositions are used as coatings to reduce friction between the surfaces of moving parts and have a vast number of applications in almost every field of engineering practice. Lubricant coatings for medical uses have special requirements. Not only must these coatings reduce friction but they must also be capable of sterilization and be biocompatible, e.g., be nontoxic and nonirritating. Examples of conventional lubricant coatings which have been used in the medical arts for years are mineral oil, petroleum jelly, and K-Y Jelly ™ (Trademark of Johnson & Johnson Co.). These lubricants while effective have not proved entirely satisfactory for every application.

For example, nasogastric and nasojejunal tubes widely used for hyperalimentation must be lubricated on their exterior surfaces to facilitate their insertion through a nasal passage, throat, or the like and to avoid damage to soft respiratory or gastrointestinal tissue. Frequently, these tubes must also have lubricated interior surfaces to facilitate movement of stylets used within the lumen of such tubes to provide sufficient rigidity to properly position a tube within a patient's body.

The term "intubation devices" is used generically herein to refer to various tubes or other devices that are lubricated for insertion into any part of a human or other animal body including blood vessels, urinary and digestive tract passages, ears and the like. Examples of intubation devices are the nasogastric and nasojejunal tubes and stylets which are more fully described in U.S. Pat. No. 4,388,076, the text of which is incorporated herein by reference.

Uniformly coating intubation devices with conventional lubricants by a physician or other person during an intubation procedure is a messy, time consuming and inefficient procedure. Obviously, manually coating the interior surfaces (lumen) of tubes and like articles is extremely difficult. Similiar difficulties are experienced with intubation devices pre-coated with conventional lubricants. Such pre-coating also increases packaging and sterilization problems experienced in the manufacture and supply of such devices.

One approach to solving the foregoing difficulties and problems has been to provide the intubation devices with hydrophilic polymer coatings. These coatings provide a thin uniform coating that is dry and non-slippery until hydrated with water. While these polymer coatings have proved effective in some situations their major drawback has been that they take too long, sometimes longer than 30 minutes, to absorb enough water to achieve sufficient lubricity for insertion into a patient. Such delays are unacceptable in many medical situations often resulting in, for example, wasted time and in some emergency cases a threat to the health of the patient.

Various attempts have been made to modify these hydrophilic polymer coatings to accelerate their ability to take up water and reach sufficient lubricity for use. However, these attempts have generally not met with complete success. For example, one attempt involved treating a hydrophilic polymer coated intubation device with sulfuric acid. This can result in serious manufacturing difficulties and toxicity problems associated with the chemical properties and high viscosity of sulfuric acid.

Certain polymer coatings based on polyvinylpyrrolidone (PVP) appear to hydrate rapidly enough but are plagued with a sliming problem. "Sliming" means that the coating becomes too soft and can be rubbed off an intubation device during ordinary use.

Accordingly, it is an object of this invention to provide a lubricant composition for coating applications which rapidly hydrates upon contact with water.

It is another object to provide a lubricant coating which has sufficient mechanical strength in a hydrated condition to resist sliming, abrasion, and the like typically experienced by intubation devices.

SUMMARY OF THE INVENTION

Briefly, the invention provides a lubricant composition comprising a hydrophilic polymer including a compound selected from the group consisting of nonionic and amphoteric surfactants wherein the compound is present in an amount sufficient to reduce the coefficient of friction of a coating of the lubricant composition to less than about 0.6 upon contact with water in less than about 5 minutes.

The invention also provides a method for coating intubation devices which involves the steps of forming a solution of hydrophilic polymer including a compound selected from the group consisting of nonionic and amphoteric surfactants; applying a coating of the solution to at least a portion of an intubation device; drying the coating and curing the hydrophilic polymer of the coating.

The invention also provides an intubation device comprising a body coated with a hydrophilic polymer including a surfactant selected from the group consisting of nonionic and amphoteric surfactants wherein the coating is characterized by being able to achieve a lubricity of less than about 0.6 upon contact with water for less than about 5 minutes.

I have discovered that the rate at which certain hydrophilic polymers take up water and attain sufficient lubricity for use in intubation procedures is accelerated without detracting from other desirable properties of the polymers by the addition of nonionic and amphoteric surfactants to the polymers.

In one of its principal aspects, the present invention provides a lubricant coating composition comprising a hydrophilic polymer and a nonionic or amphoteric surfactant, present in an amount effective to reduce the coefficient of friction of the composition to less than about 0.6 in less than about 5 minutes upon contact with water. Preferably, the hydrophylic polymer is a polyurethane, the surfactant is nonionic and the coefficient of friction is reduced to less than about 0.2 in less than about one minute and more preferably a coefficient of friction less than about 0.1 in less than about 5 to 10 seconds.

In another of its aspects the present invention provides an intubation device, such as the nasogastric tube, coated with a hydrophilic polymer includin9 an amount of nonionic or amphoteric surfactant effective to reduce the coefficient of friction of the hydrophylic polymer to less than 0.6 in less than 5 minutes upon contact with water.

In yet another aspect the present invention provides a method for coating intubation devices which comprises the steps of coating the intubation device with a hydrophilic polymer solution including an amount of nonionic or amphoteric surfactant effective to reduce the coefficient of friction of the hydrophylic polymer to less than about 0.6 in less than about 5 minutes upon contact with water and drying the coating at sufficient temperatures to cure the polymer. In a preferred embodiment the intubation device is provided with an additional outer coat of hydrophilic polymer that does not include a surfactant.

DETAILED DESCRIPTION OF THE INVENTION

Figure 1:
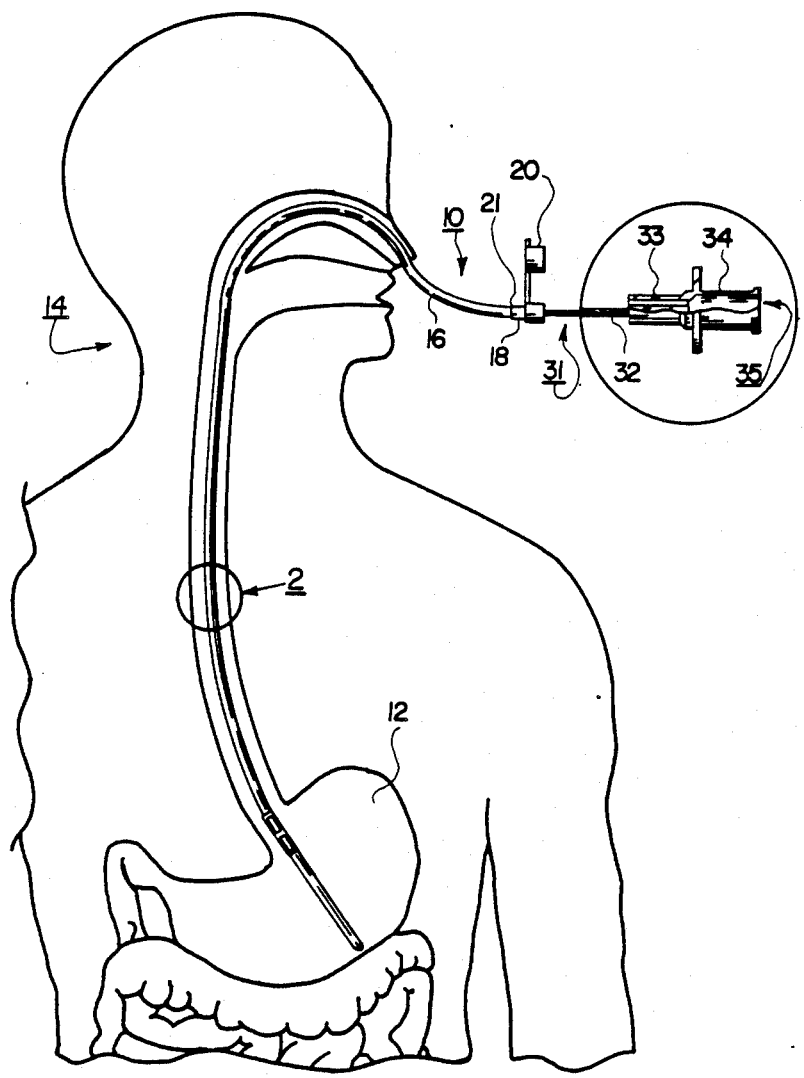
FIG. 1 is a fragmentary cross-sectional view of a nasogastric tube inserted in a human patient.

The terms "nonionic and amphoteric surfactant" as used herein mean any surface active agent which accelerates the hydration of hydrophilic polymer coatings of the present invention; so that these coatings rapidly achieve their lubricating properties (low coefficient of friction) when contacted with water without detracting from the polymer's other desirable properties. While the physical mechanism whereby such rapid hydration is achieved is not fully understood it is believed that the sufactants lower the interfacial tension between the polymers and hydrating water molecules thus permitting the water to more readily access the hydrophilic functional groups on the polymer.

Surfactants particularly useful in the practice of this invention include conventional nonionic surfactants, such as, linear alkyl sulfonates, alkylphenyl hydroxypolyoxyethylenes, polyethylene glycol ethers and octylphenoxy polyethoxyethanol. These surfactants can be made by techniques well known in the art and many are commercially available from established suppliers, e.g., TEGRITOL ® nonionic surfactants available from Union Carbide Corporation, of Danbury, Ct., U.S.A. are alkylphenyl hydroxypolyoxyethylenes and more particularly, nonylphenol polyethylene glycol ethers, having average molecular weights in the range of about 350 to 2000.

Triton ® X-100 (octylphenoxypolyethoxyethanol) is a surfactant commercially available from Rohm and Haas Company of Philadelphia, Pa., U.S.A., and is the presently preferred surfactant for purposes of the present invention.

The term "hydrophilic polymer" as used herein means a water absorbing polymer that has lubricating properties, i.e., a coefficient of friction less than about 0.60, preferably less than about 0.20 and more preferrably less than about 0.10, when in the hydrated or partially hydrated condition.

A particularly useful class of hydrophilic polymers are the polyurethanes derived from polyethylene glycols, polypropylene glycol or polyalkylene amines reacted under conditions known in the art with isocyanates such as toluene diisocyanates, methylene bis(4-cyclohexylisocyanate) or urethane forming isocyanate equivalents.

Another useful class of hydrophilic polymers are the lower alkyl, or alkoxy alkyl, esters or amides of acrylic or methacrylic acid. An example of a useful hydrophilic acrylic polymers are the HYDRON TM polymers of National Patent Development Corp., New York, N.Y., U.S.A.

The hydrophilic polyurethanes, such as those more fully described in U.S. Pat. Nos. 3,822,238 and 3,975,350, each of which is incorporated herein by reference, are preferred for many applications due to their high mechanical strength, resistance to chemical attack and low toxicity, e.g., compatibility with acids and the like found in the human stomach.

The preferred hydrophilic polymer for use in coatings for nasogastric tubes, as herein described, is a hydroxy-terminated hydrophilic polyurethane having an average molecular weight of about 7,500 which is the product of polyethylene glycol having an average molecular weight of 1890–1900 and methylene bis(4-cyclohexylisocyanate) reacted in the presence of a small amount of urethane forming catalyst, such as, stannous octoate.

Figure 2:
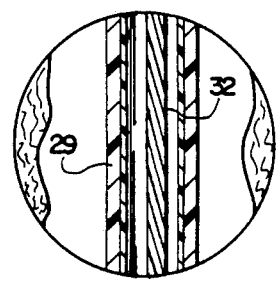
FIG. 2 is an exploded fragmentary view of a section of the nasogastric tube in FIG. 1.
Figure 3:
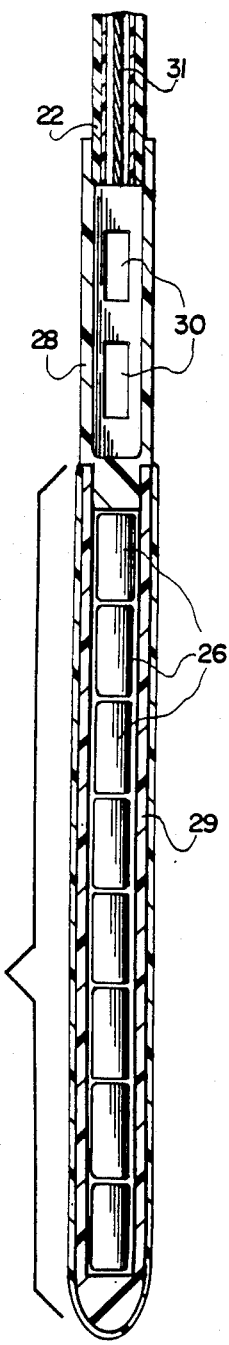
FIG. 3 is an exploded fragmentary view of the bolus portion of the nasogastric tube of FIG. 1.

FIGS. 1, 2 and 3 illustrate an intubation device in the form of a nasogastric intubation device 10 coated with a lubricant composition for insertion into a stomach 12 of human patient 14. The nasogastric incubation device 10 comprises a flexible tube 16 made of any material conventionally used for such tubes such as polyurethane, polyethylene or polyvinylchloride having an inside diameter of 0.08 inch and outside diameter of 0.108. The sizes of such tubes are typically designated in French units. Sizes 5–12 French are preferred for nasogastric tubes and 8 French is most preferred. The coatings of this invention may be of any thickness required for a particular application. However, coatings for nasogastric tubes are preferably about 0.5 to 2.5 mils thick.

A connector such as a female luer 18 connector provided with closure cap 20 is affixed to a proximal end 21 of the flexible tube 16 and a bolus 24 is provided at the distal end 22 of the flexible tube 16. The bolus 24 has a plurality of titanium weights 26 disposed therein for aiding in positioning, and maintaining the position, of the flexible tube 16 in the patient. The bolus 24 is connected to the flexible tube 16 with a connector 28 provided with a plurality openings 30 therein for permitting the passage of fluid into or out of the tube.

Stylet 31 comprises a wire body 32, preferably stainless steel, having a distal end provided with an enlarged ball (not shown). The enlarged ball may comprise a tightly wound ball of wire. Proximal end 21 of the wire body 32 is affixed to a plug 34, which is preferably hollow and provided with means such as a tubular passage 35 for permitting fluid to flow into and out of the flexible tube 16. Means for accurately positioning and securing the stylet 32 in the flexible tube 16, such as a male luer fitting 33 that cooperates with female luer 18 is also provided. The connectors 18 and 28, plu9 34, cap 20, and like parts may be formed from any suitable material such as polyethylene, polypropylene or polyvinylchloride.

The flexible tube 10, bolus 24 and connector 28 are provided with a lubricant coating 29 (FIG. 3) comprising a hydrophilic polymer including a compound selected from the group consisting of nonionic and amphoteric surfactants. The surfactant is provided in an amount effective to cause the lubricant coating to rapidly hydrate upon contact with water so that it has sufficient lubricity for intubation procedures in less than about 5 minutes. It will be appreciated that almost any number of such lubricant coatings may be provided as necessary or desired.

Figure 4:
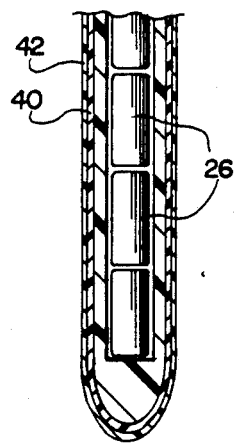
FIG. 4 is an exploded view of the extreme end portion of a nasogastric tube.

FIG. 4 shows an alternative embodiment wherein the nasogastric tube 10 is coated with a first layer 40 of hydrophilic polymer which includes a compound selected from the group consisting of nonionic and amphoteric surfactants that accelerate hydration of the polymer. A second layer 42 of hydrophilic polymer that does not include one of the specified surfactants capable of accelerating hydration of the polymer is applied over the first layer 40. An advantage of this two layer system is prolonged lubricity which facilitates removal and reinsertion of the tube.

An embodiment of the present invention is described in the following Example for purposes of illustration and further description and as such the Examples should not be construed to limit the invention in any way.

EXAMPLE 1

A hydroxy-terminated hydrophilic polyurethane having an average molecular weight of about 7500, was prepared by reacting about 87.68 grams (gm) of polyethylene glycol having an average molecular weight of 1890–1900 with about 12.31 gm methylene bis(4-cyclohexylisocyanate) in the presence of about 0.12 gm stannous octoate catalyst.

A first coating composition was prepared by dissolving about 6 gm of a polymer prepared as described above in about 200 gm of a 75 parts methylene bichloride/25 parts ethyl alcohol solution and adding about 40 gm of TRITON-X-100 ®(octylphenoxy-polyethoxyethanol) surfactant. It will be appreciated by those skilled in the art that solvent systems other than methylene bichloride and alcohol are useful in the practice of this invention and that preferred systems will include a component for preparing a surface to be coated for forming a strong adhesive bond with the polymer coating and for solublizing the polymer, e.g., 75 parts tetrahydrofuran and 25 parts alcohol.

A second coating composition without a nonionic or amphoteric surfactant capable of accelerating hydration of the polymer was then prepared by dissolving about 2 gms of a polymer prepared as described above in 100 gm of 75 parts methylene bichloride/25 parts ethyl alcohol solvent.

EXAMPLE 2

A first coating of the first coating composition with surfactant, described in Example 1, was applied to a plastic tube suitable for an intubation device by submerging the tube in the first coating composition for about 15 seconds; withdrawing the tube at a rate of about 15 inches per minute and then air drying the coated tubing for about 5 minutes followed by oven drying at 100° C. for about 10 minutes to cure the first coating.

The tube having the cured first coating was cooled to room temperature, submerged in the second coating composition containing no surfactant, described in Example 1, for about 15 seconds, and then slowly withdrawn at a rate of about 15 inches per minute to produce a second coating. The second coating was air dried for about 5 minutes, cured in a circulating oven for about 10 minutes at 100° C. and cooled to room temperature. The finished tubing had a multi-layer (two layer) coating, the first (inside) layer being hydrophilic polymer containing surfactant and the second (outside) layer being hydrophilic polymer only.

Upon contact with water, the multi-layer coated tubing very rapidly became lubricated and absorbed water as indicated by the very slippery feel of the tubing surfaces and within a few minutes the coefficient of friction of the tubing surface was reduced to less than about 0.1. Notably, the interior or lumen of the tube also became lubricated as indicated by the easy movement of a stylet within the tube even when the tube was twisted into complex shapes.

An important advantage of the multi-coating procedure is an observed reduction of the rate at which surfactant is released from the coatings into the patient so that such tubes retain their ability to hydrate rapidly over longer in-use periods and thus are often reusable.

The polymer compositions prepared in accordance with the present invention may be applied as thin, e.g. less than about 2.5 mil, coatings which when contacted with excess water become sufficiently lubricated for use in intubation procedures in less than about 5 minutes and more preferably less than about 5 to 10 seconds. Similar coatings which do not include surfactants as described herein have been observed to take 10 to 30 minutes to achieve adequate lubricity.

What is claimed is:

1. An intubation device having a body and a coating on at least a portion of said body, said coating including an effective amount of a hydrophilic polymer and a compound selected from the group consisting of nonionic and amphoteric surfactants, said compound being present in an amount effective to reduce the coefficient of friction of said coating to less than about 0.6 upon contact with water in less than about 5 minutes.

2. The intubation device of claim 1 wherein the coefficient of friction is reduced to less than about 0.2 in less than about 5 to 10 seconds.

3. The intubation device of claim 2 wherein said polymer is a hydrophilic polyurethane.

4. The intubation device of claim 3 wherein said polyurethane is hydroxy-terminated and comprises the reaction product of:
   (A) polyethylene glycol, and
   (B) methylene bis (4-cyclohexylisocyanate); and said compound is a nonionic surfactant.

5. The intubation device recited in claim 4 wherein said polyurethane has an average molecular weight of about 7500 and said polyethylene glycol has an average molecular weight of about 1890 to 1900.

6. The intubation device of claim 5 wherein said surfactant is octylphenoxy polyethoxyethanol.

7. The intubation device in claim 5 wherein said surfactant is a linear alkyl sulfonate.

8. The intubation device of claim 5 wherein said surfactant is an alkylphenylhydroxypolyoxyethylene.

9. The intubation device of claim 5 wherein said surfactant is a nonylphenol polyethylene glycol ether having an average molecular weight of about 350 to 2000.

10. The intubation device recited in claim 1 wherein said body comprises a nasogastric tube.

11. The intubation device recited in claim 6 wherein said body comprises a nasogastric tube.

12. The intubation device recited in claim 7 wherein said body comprises a nasogastric tube.

13. The intubation device recited in claim 4 wherein said body comprises a nasogastric tube.

14. The intubation device recited in claim 5 wherein said body comprises a nasogastric tube.

15. A method for coating an intubation device with a lubricating composition comprising the steps of:
  forming a hydrophilic polymer solution including a compound selected from the group consisting of nonionic acid amphoteric surfactants wherein said compound is present in an amount effective to reduce the coefficient of friction of a dry surface of the composition to less than about 0.6 in less than about 5 minutes upon contact with water; and
  applying the solution to at least a portion of an intubation device to form a first coating; and
  subsequently drying and curing the coating.

16. The method of claim 15 further comprising the step of applying a coating of hydrophilic polymer on said portion of the intubation device prior to applying said first coating thereover.

17. The method of claim 15 wherein said polyurethane is hydroxy-terminated and comprises the reaction product of:
  (A) polyethylene glycol, and
  (B) methylene bis (4-cyclohexylisocyanate); and said compound is a nonionic surfactant.

18. The method of claim 17 wherein said polyurethane has an average molecular weight of about 7500 and said polyethylene glycol has an average molecular weight of about 1890 to 1900.

19. The method of claim 17 wherein said surfactant is octylphenoxy polyethoxyethanol.

20. The method of claim 17 wherein said surfactant is a linear alkyl sulfonate.

21. The method of claim 17 wherein said surfactant is an alkylphenylhydroxypolyoxyethylene.

22. The method of claim 17 wherein said surfactant is a nonylphenol polyethylene glycol ether having an average molecular weight of about 350 to 2000.

* * * * *

UNITED STATES PATENT AND TRADEMARK OFFICE
CERTIFICATE OF CORRECTION

PATENT NO. : 4,705,709

DATED : November 10, 1987

INVENTOR(S) : VINCENT L. VAILLANCOURT

It is certified that error appears in the above-identified patent and that said Letters Patent is hereby corrected as shown below:

```
In the Abstract, line 2 "hydrophylic" should be -hydrophilic-
Column 2, line 11 "polyvinylpyrroli" should be -polyvinylpyrroli-
Column 2, line 60 "hydrophylic" should be -hydrophilic-
Column 3, line 2 "hydrophylic" should be -hydrophilic-
Column 3, line 10 "hydrophylic" should be -hydrophilic-
Column 4, line 8 cancel "a"
Column 4, line 50 "plurality" should be -plurality of-
Column 4, line 62 "plu9" should be -plug-
Column 7, line 3 "claim 4" should be -claim 8-
Column 7, line 5 "claim 5" should be -claim 9-
```

Signed and Sealed this

Nineteenth Day of July, 1988

*Attest:*

DONALD J. QUIGG

*Attesting Officer*  *Commissioner of Patents and Trademarks*